United States Patent [19]

Mallon

[11] 4,447,632

[45] May 8, 1984

[54] PROCESS FOR PRODUCTION OF ALKYL SILICATES FROM SILICON METAL

[75] Inventor: Charles B. Mallon, Belle Mead, N.J.

[73] Assignee: Union Carbide Corporation, Danbury, Conn.

[21] Appl. No.: 485,822

[22] Filed: Apr. 18, 1983

[51] Int. Cl.$^3$ ............................ C07F 7/18; C07F 7/04
[52] U.S. Cl. .................................................. 556/470
[58] Field of Search ........................................ 556/470

[56] References Cited

U.S. PATENT DOCUMENTS

| | | | |
|---|---|---|---|
| 2,473,260 | 6/1949 | Rochow | 260/448.8 |
| 2,727,054 | 12/1955 | Wright | 260/448.8 |
| 2,822,348 | 2/1958 | Haslam | 260/75 |
| 2,881,198 | 4/1959 | Bailey et al. | 260/448.8 |
| 2,927,937 | 3/1960 | Gaines | 260/448.8 |
| 4,185,029 | 1/1980 | Kreuzburg et al. | 556/470 |
| 4,211,717 | 7/1980 | Emblem et al. | 556/470 |
| 4,288,604 | 9/1981 | Magee et al. | 556/470 |
| 4,323,690 | 4/1982 | Montle et al. | 556/470 |

FOREIGN PATENT DOCUMENTS

| | | | |
|---|---|---|---|
| 577858 | 6/1959 | Canada | 556/470 |
| 55-149290 | 11/1980 | Japan | 556/470 |
| 630644 | 10/1949 | United Kingdom | 556/470 |
| 1110957 | 4/1968 | United Kingdom | 556/470 |
| 757536 | 5/1978 | U.S.S.R. | 556/470 |

*Primary Examiner*—Paul F. Shaver
*Attorney, Agent, or Firm*—Bernard Francis Crowe

[57] ABSTRACT

Ethyl orthosilicate is produced by contacting silicon metal with a mixture of methanol and ethanol in the presence of a catalytic amount of an alkali metal carbonate or bicarbonate at a temperature of at least 130° C. The methyl orthosilicates produced are converted to ethyl orthosilicate by transesterification with ethanol.

8 Claims, No Drawings

PROCESS FOR PRODUCTION OF ALKYL SILICATES FROM SILICON METAL

FIELD OF THE INVENTION

This invention pertains to the production of alkyl silicates from silicon metal and more particularly to the reaction of silicon metal with alcohols.

DESCRIPTION OF THE PRIOR ART

Alkyl silicates are known in the art comprising unhydrolyzed alkyl and alkoxy alkyl silicates and alkyl and alkoxy alkyl silicates hydrolyzed up to 100%. Alkyl silicates are produced by the reaction of silicon tetrachloride (and other halides of silicon) with alcohols and alkoxy alcohols, generally in a reactor equipped with a stirrer, condenser, and vat scrubber. The hydrogen chloride by-product is removed by reflux which may be carried out at reduced or atmospheric pressure. Through this process the most common products TEOS (tetraethyl orthosilicate) and Cellosolve ® silicate are made. Cellosolve is a trademark of Union Carbide Corporation for monoalkyl ethers of ethylene glycol. The preparation of alkyl silicates from silicon tetrachloride and an alcohol suffers from the fact that the hydrogen chloride produced is extremely corrosive.

Subsequently these products may be hydrolyzed by the addition of water and an acid catalyst. The amount of water added determines the degree of hydrolysis in the final product. Commercially available products derived from ethanol include the unhydrolyzed TEOS, Condensed Ethyl Silicate (about 7% hydrolysis), and Ethyl Silicate 40 (40% hydrolysis containing 40% $SiO_2$).

The uses of ethyl orthosilicate derive from its ability to form silica and alcohol. Partially hydrolyzed ethyl orthosilicates are the basis of silicate paints, and are used for sealing and weatherproofing porous stone and also as binders in the investment casting of metals. Completely hydrolyzed ethyl orthosilicate provides a colloidal sol of silica suitable for the preparation of fluorescent powders. These silicate esters have also found wide use in conjunction with metals such as zinc powder in providing zinc-rich coatings effective in protecting steel against corrosion.

A more facile method for the production of alkyl silicates is based on the reaction of the silicon metal with alcohols catalyzed by alkali alkoxides, alkali carboxylates and copper and/or nickel salts to catalyze this reaction.

The production of alkyl silicates directly from silicon metal entails some undesirable features, primarily due to the use of catalysts that are expensive, difficult to store and handle and/or difficult to prepare.

It is, therefore, an object of this invention to provide a method for the production of alkyl silicates free of the undesirable features of the prior art.

Other objects will become apparent to those skilled in the art upon a further reading of the specification.

SUMMARY OF THE INVENTION

It has now been found that the reaction of silicon metal with alcohols to produce alkyl silicates at a temperature of at least about 130° C. can be catalyzed by alkali carbonates and bicarbonates. Preferred alkali carbonates or bicarbonates include those where the cation moiety is sodium, potassium, or lithium. The preferred temperature is about 175°–185° C.

The invention is limited to alkali metal carbonates or bicarbonates since the corresponding alkaline earth carbonates or bicarbonates are ineffective as catalysts in this reaction.

While alkali metal hydroxides also function as catalysts in this reaction, their highly corrosive nature renders them unsuitable from both a safety and economical viewpoint.

This invention is further limited in that the preferred alkyl silicate, viz., ethyl orthosilicate is best made through the reaction of methanol or a mixture of methanol and ethanol containing at least 10% methanol by weight with silicon metal followed by transesterification of the resultant methyl orthosilicates to afford the desired ethyl orthosilicate. It is somewhat unexpected that in this homologous series of saturated aliphatic alcohols, the activity of the first member, methanol, is much greater than that of the higher aliphatic alcohols. While propyl and higher saturated aliphatic alcohols can also be used in the transesterification, there is not much commercial demand for this type of product since ethyl orthosilicate seems to be the desired alkyl silicate from the point of view of the end uses referred to above.

The invention is further described in the examples which follow. All parts and percentages are by weight unless otherwise specified.

EXAMPLES 1–7

All reactions were run in a 1 liter high-pressure reactor equipped with a variable speed agitator, electric heater, internal cooling coil, thermocouple and vent valve. The alcohols were charged to the reactor initially, followed by the catalyst and metallic silicon. The reactor was then sealed, the stirrer set at 1500 rpm, and the heater turned on. Temperature and pressure were recorded at appropriate times, generally when the pressure reached 650–700 psi, at which point the vent valve was opened until the pressure was reduced to 450–500 psi. Some alcohols and silicates were lost during these ventings, but for the silicates the total amount was negligible. At the end of the reaction time, the reactor contents were cooled, the reactor vented and opened, and the product discharged. Unreacted silicon was removed by filtration and weighed, and the product mixture was analyzed by gas chromatography, using hexadecane as an internal standard. All five expected products were observed by gas chromatographic analysis in experiments using ethanol/methanol mixtures (i.e., $(CH_3O)_4Si$, $(CH_3O)_3SiOC_2H_5$, $(CH_3O)_2Si(OC_2H_5)_2$, $CH_3OSi(OC_2H_5)_3$ and $(C_2H_5O)_4Si$. Silicate yields reported are the sums of the molar yields of these individual silicates, plus the dimers often observed by gas chromatography.

The results of seven examples in which potassium carbonate was used as the catalyst at levels ranging from 0.1 gram to 10 grams together with a mixture of 250 grams each of methanol and ethanol at a temperature of 180±5° C. are summarized in Table 1. Reaction times, the weight of silicon metal charged and silicon metal recovered, as well as the moles of silicate produced are also delineated in Table 1.

As shown by the data in Table 1, potassium carbonate is an effective catalyst for the reaction of silicon metal with methanol and ethanol at levels ranging from 0.1 gram to 10 grams of potassium carbonate per 500 grams of alcohol.

The mesh sizes given for the silicon metal used in the reaction are standard U.S. sieve sizes.

EXAMPLES 8-12—COMPARISON OF CATALYSTS

Using the procedure described in Example 1, the reaction of silicon metal with methanol and ethanol was carried out in the presence of several different catalysts. The data presented in Table 2 show that potassium carbonate, potassium hydroxide, sodium carbonate, and sodium bicarbonate are all capable of catalyzing this reaction. Calcium carbonate, however, is completely ineffective as a catalyst. This demonstrates the inapplicability of alkaline earth carbonates as a catalyst for this reaction.

EXAMPLES 13-14—EFFECT OF ALCOHOL COMPOSITION

Using the procedure described in Example 1, the reaction of silicon metal with alcohols was demonstrated with a 50—50 mixture of ethanol and methanol and again with ethanol alone. The reaction conditions for these examples were identical including the use of 10 grams of potassium carbonate as a catalyst, a reaction time of 4.5 hours, 60 grams of silicon metal (325 mesh) and a reaction temperature of 180±5° C. As can be seen from the data in Table 3, potassium carbonate is an excellent catalyst when the alcohol reactant is a mixture of ethanol and methanol, but is not a catalyst for ethanol alone.

TABLE I

Effect of Potassium Carbonate Concentration

| Example | $K_2CO_3$ | Reaction Time | Si wt., mesh | Si Recovered | Moles Silicate Produced |
|---|---|---|---|---|---|
| 1 | 10 g | 4.5 hrs | 60 g (−325) | 31 g | 0.80 |
| 2 | 10 g | 4.5 hrs | 60 g (−100) | 23 g | 0.64 |
| 3 | 5 g | 4.5 hrs | 60 g (−100) | 35 g | 0.67 |
| 4 | 2.5 g | 4.5 hrs | 60 g (−100) | 37 g | 0.56 |
| 5 | 1.0 g | 4.5 hrs | 30 g (−325) | 22 g | 0.22 |
| 6 | 0.5 g | 3.8 hrs | 30 g (−325) | 10 g | 0.29 |
| 7 | 0.1 g | 2.3 hrs | 30 g (−325) | 12 g | 0.24 |

Note: The minus sign (−) appearing before the mesh size indicates that the particles passed through a sieve with the indicated mesh size.

TABLE II

Comparison of Catalysts

| Example | Catalyst (wt., g.) | Reaction Time, hrs. | Si wt., g (mesh) | Si Recovered g. | Moles Silicate Produced |
|---|---|---|---|---|---|
| 8 | $K_2CO_3$ (1) | 4.5 | 30 (−325) | 22 g | 0.22 |
| 9 | KOH (1) | 3.5 | 30 (−325) | 13 g | 0.46 |
| 10 | $Na_2CO_3$ (5) | 2.0 | 30 (−100) | 23 g | 0.26 |
| 11 | $NaHCO_3$ (5) | 2.2 | 30 (−100) | 25 g | 0.19 |
| 12 | $CaCO_3$ (5) | 2.0 | 30 (−325) | — | 0 |

TABLE III

Effect of Alcohol Composition

| Example | Ethanol/Methanol | Moles Silicate Produced |
|---|---|---|
| 13 | 250 g/250 g | 0.80 |
| 14 | 500 g/0 g | 0.0 |

EXAMPLE 15—EFFECT OF REACTION TEMPERATURE

A run was made using silicon metal (30 grams, 325 mesh), potassium carbonate (5 grams), methanol (250 grams) and ethanol (250 grams) in which the reaction temperature was varied to determine the lowest temperature at which the reaction occurred. Progress of the reaction was determined by the pressure increase resulting from the evolution of hydrogen, a reaction by-product. It was found that pressure increases could be easily detected at temperatures as low 130° C., but that little or no reaction could be detected at 120° C. Therefore, the temperature for operating the method of this invention should be 130° C. or greater.

EXAMPLE 16—Transesterification

Since there is not a commercial demand for methyl orthosilicate, any silicate containing methyl groups should be converted to ethyl orthosilicate which is an article of commerce. In order to demonstrate this, the following transesterification reaction was run. 10 Grams of methyl orthosilicate was charged to a reaction vessel fitted with a stirrer, thermometer, and a distillation head. Sulfuric acid catalyst (0.1 gram) was also charged together with 50 grams of ethanol. The reaction mixture was heated to reflux and then methanol and ethanol were distilled off at a temperature of about 64°-78° C. The residue was identified by gas chromatography as consisting of ethyl orthosilicate.

Although the invention has been described with a certain degree of particularity, it is understood that the present disclosure of the preferred forms has been made only by way of example and that numerous changes can be resorted to without departing from the spirit and the scope of the invention.

I claim:

1. Process for production of alkyl silicates from silicon metal which comprises contacting finely divided silicon metal with a mixture of methanol and ethanol containing at least 10% methanol by weight at a temperature of at least about 130° C. in the presence of a catalytic amount of a carbonate or bicarbonate of an alkali metal until methyl orthosilicate, ethyl orthosilicate and mixtures of methyl ethyl silicates are formed.

2. Method claimed in claim 1 wherein the methyl orthosilicates are subjected to transesterification with ethanol until said methyl orthosilicates are converted to ethyl orthosilicate.

3. Method claimed in claim 1 wherein the catalyst is potassium carbonate.

4. Method claimed in claim 1 wherein the catalyst is sodium carbonate.

5. Method claimed in claim 1 wherein the catalyst is lithium carbonate.

6. Method claimed in claim 1 wherein the catalyst is sodium bicarbonate.

7. Method claimed in claim 1 wherein the temperature is about 175° to about 185° C.

8. Process claimed in claim 1 wherein the ratio of methanol to ethanol is about 50/50 by weight.

* * * * *